US00PP12113P2

(12) United States Plant Patent
Walden

(10) Patent No.: US PP12,113 P2
(45) Date of Patent: Oct. 2, 2001

(54) MINIATURE ROSE PLANT NAMED 'JACIRAPS'

(75) Inventor: John K. Walden, Burlington, WA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 09/455,226

(22) Filed: Dec. 6, 1999

(51) Int. Cl.[7] ..... A01H 5/00
(52) U.S. Cl. ..... Plt./116

(58) Field of Search ..... Plt./116, 121, 123, Plt./127

*Primary Examiner*—Howard J. Locker
(74) *Attorney, Agent, or Firm*—Klarquist Sparkman Campbell Leigh & Whinston, LLP

(57) ABSTRACT

A miniature rose plant having compact plant habit; novel, bright pink and white, bicolor flowers, the petals each having a yellow color spot on their lower portions which present a multi-pointed star shape in the center of a flower when it first opens; sweet, spicy fragrance; and dark green, glossy foliage, resistant to powdery mildew, blackspot and rose rust.

1 Drawing Sheet

The present invention relates to a new and distinct variety of rose plant of the miniature class which was originated by me by crossing the variety 'JACimin' (U.S. Plant Pat. No. 8,850), with an unnamed seedling.

The primay objective of this breeding was to produce a dwarf, compact and low growing garden rose with bright pink and white bicolor flowers, a light fragrance, dark green, glossy, disease resistant foliage and flowers borne in large clusters. The objective was substantially achieved, along with other desirable improvements, as evidenced by the following unique combination of characteristics that are outstanding in the new variety and that distinguish it from its parents, as well as from all other varieties of which I am aware:

1. Dwarf, compact habit (14 to 18 inches tall and 18 to 20 inches wide);
2. Novel, bright pink and white bicolor flower, the petals each having a yellow spot on their lower portions which present a multi-pointed star shape in the center of the flower when it first opens;
3. Slight, spicy fragrance;
4. Dark green, glossy foliage; and
5. Resistance to powdery mildew and rose rust.

Asexual reproduction of this new variety by cuttings, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—'JACimin' (U.S. Plant Pat. No. 8,850).

*Pollen parent.*—Unnamed seedling (unnamed seedling×MORpints).

Classification:

*Botanical.*—*Rosa hybrida.*

*Commercial.*—Miniature rose.

FLOWER

Observations made in September, 1999, from specimens grown in a garden environment at Somis, Calif.

Blooming habit: Continuous.

Bud:

*Size.*—About ¾ inch long when the petals start to unfurl.

*Form.*—The bud form is short, pointed ovoid.

*Color.*—When sepals first divide, bud color is predominantly Red-Purple Group 63A, blending with Red-Purple Group 73D. When half blown, the upper sides of the petals are Red-Purple Group 57B on the outer half, blending to Yellow Group 11D on the inner half; and the lower sides of the petals are between Red-Purple Group 65B and Red-Purple Group 65C on the outer half to two-thirds, blending to Yellow Group 4D on the inner part of the petal.

*Sepals.*—Color: Yellow-Green Group 146C, with some bronzing of Greyed-Red Group 178B. Surface texture: Lightly hairy and glandular. There are three normally appendaged sepals. There are two unappendaged sepals with hairy edges.

*Receptacle.*—Color: Between Yellow-Green Group146B and Yellow-Green Group 146C. Shape: Funnel. Size: Small (about ¼ inch×¼ inch). Surface: Hairy.

*Peduncle.*—Length: Short (about ⅞ inch). Surface: Rough, glandular. Color: Yellow-Green Group 144B with bronzing of Greyed-Red Group 178B where exposed to direct sunlight. Strength: Stiff; erect.

Bloom:

*Size.*—Small. Average open size is 2½ inches.

*Borne.*—Singly and several together in pyramidal clusters of three to seven blooms.

*Stems.*—Strength: Normal. Average length is about six to eight inches.

*Form.*—When first open: Bloom is slightly cupped. Permanence: Flattens; outer petal edges curl very slightly.

*Petalage.*—Number of petals under normal conditions: 15 to 20.

*Color.*—The upper sides of the petals are Red-Purple Group 58D on the outer half, blending to Yellow Group 4D on the inner half. The reverse sides of the petals are Red-Purple Group 65C on the outer ⅔, blending to Yellow Group 4D at the inner ⅓ of the petal. The base of each petal has a Yellow Group 1C ⅛ inch×⅛ inch spot at its point of attachment. The major color on the upper side is Red-Purple Group 58D.

*Discoloration.*—The general tonality at the end of the first day: Unchanged. At the end of the third day: Near Red-Purple Group 68B. With further aging, there is decreasing intensity toward Red-Purple Group 68D.

*Fragrance.*—Slight; spicy and sweet.

Petals:

*Texture.*—Thin.

*Shape.*—Pointed; deltoid.

*Form.*—Flat with tips slightly recurved.

*Arrangement.*—Imbricated (regularly arranged). Petaloids in the center are few (0 to 3); small.

*Persistence.*—Petals drop off cleanly before drying.

*Lastingness.*—On the plant: Fair (about five to six days). As a cut flower: Not tested.

Reproductive parts:

*Anthers.*—Size: Large. Quantity: Many. Color: Yellow Group 12B. Arrangement: Regular around styles.

*Filaments.*—Color: Yellow Group 3C.

*Pollen.*—Color: Near Yellow Group 11A.

*Styles.*—Color: Yellow-Green Group 146C.

*Stigmas.*—Color: Between Yellow-White Group 158A and Yellow-White Group 158B.

Plant:

*Form.*—Bush.

*Growth.*—Vigorous; dwarf; upright; branching. At maturity, height is 14 to 18 inches, width is 18 to 20 inches.

Foliage: Number of leaflets on normal mid-stem leaves: Five or seven.

*Size.*—Small (3⅛ inches long×1⅞ inches wide).

*Quantity.*—Normal.

*Color.*—New foliage: Upper and lower surfaces: Greyed-Purple Group 183A, rapidly turning green. Old foliage: Upper surface: Green Group 137B. Lower surface: Yellow-Green Group 146B.

Leaflets:

*Shape.*—Oval.

*Texture.*—Leathery; glossy; smooth.

*Edge.*—Serrated.

*Serration.*—Double.

*Petiole rachis.*—Color: Yellow-Green Group 146C; Greyed-Red Group 178B near edge.

*Petiole underside.*—Rough, with prickles and many glandular structures.

*Stipules.*—Short (about ⅜ to 9/16 inch long); lightly bearded.

*Disease resistance.*—Resistant to mildew, blackspot and rust under normal growing conditions.

Wood:

*New wood.*—Color: Yellow-Green Group 146C mixed with Greyed-Red Group 178A. Bark: Smooth.

*Old wood.*—Color: Yellow-Green Group 146B. Bark: Smooth.

Prickles:

*Quantity.*—On main canes from base: Ordinary. On laterals from main canes: Ordinary.

*Form.*—Medium (⅜ inch); hooked downward.

*Color when young.*—Greyed-Orange Group 166B.

*Color when mature.*—Between Greyed-Orange Group 165A and Greyed-Orange Group 165B.

Small prickles:

*Quantity.*—On main stalks: None. On laterals: None.

I claim:

1. A new and distinct variety of rose plant of the miniature class, substantially as herein shown and described, characterized particularly by its compact plant habit; novel, bright pink and white, bicolor flowers, the flowers each having a yellow color spot on their lower portions which present a multi-pointed star shape in the center of a flower when it first opens; sweet, spicy fragrance; and dark green, glossy foliage, resistant to powdery mildew, blackspot and rose rust.

* * * * *

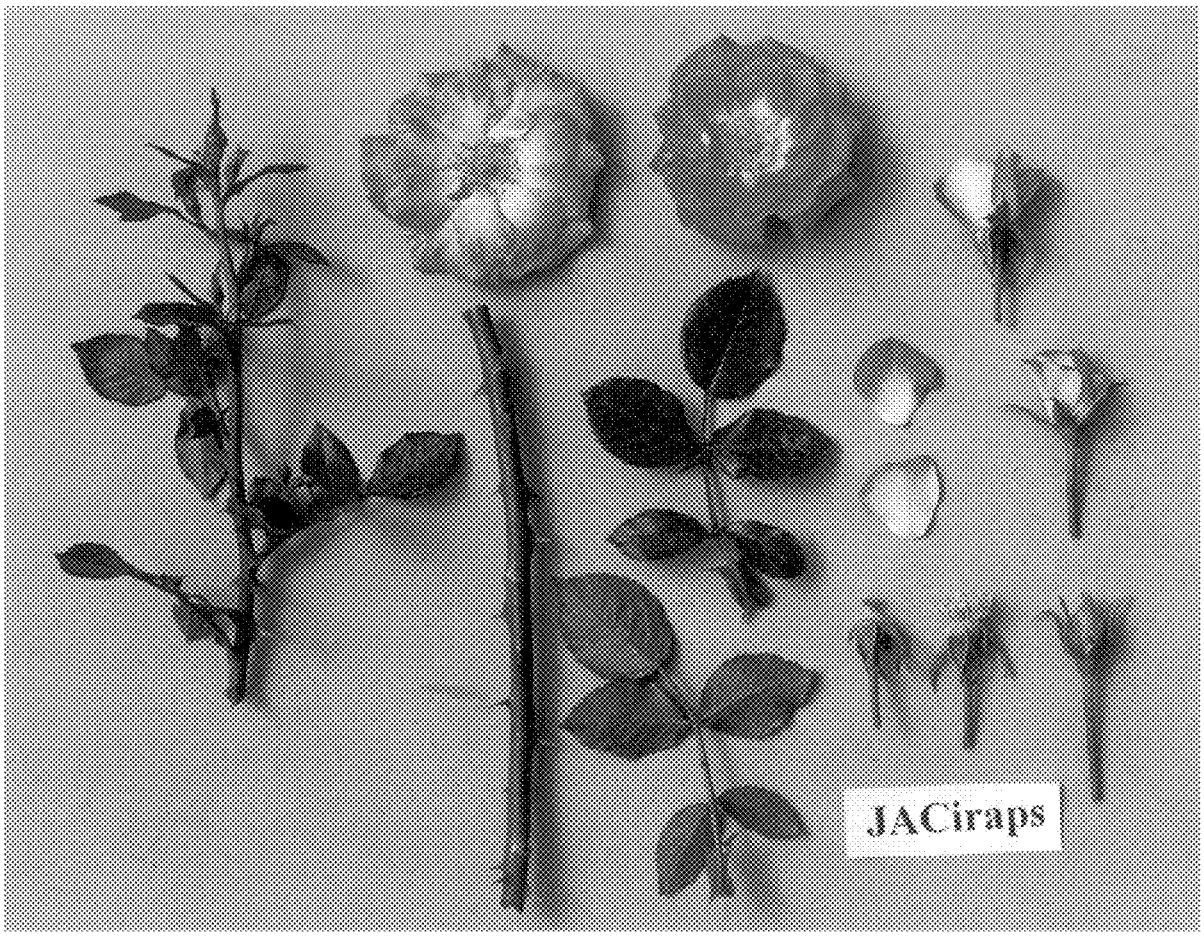
JACiraps